United States Patent [19]

Bryman

[11] Patent Number: 5,493,025
[45] Date of Patent: Feb. 20, 1996

[54] PROCESS FOR PREPARATION OF FLUORINATED BETA-KETO ESTER

[75] Inventor: Lois M. Bryman, North Wales, Pa.

[73] Assignee: Rohm and Haas Company, Philadelphia, Pa.

[21] Appl. No.: 281,372

[22] Filed: Jul. 27, 1994

[51] Int. Cl.⁶ .................... C07D 239/26; C07C 69/716
[52] U.S. Cl. ........................... 544/242; 560/174
[58] Field of Search .................. 560/174; 544/242

[56] References Cited

U.S. PATENT DOCUMENTS 5,300,477  4/1994  Tice .......................... 504/242

FOREIGN PATENT DOCUMENTS 931689  7/1963  United Kingdom .

OTHER PUBLICATIONS

Streitweiser et al., "Introduction to Organic Chemistry," Macmillan Publishing Co., Inc., New York, pp. 1110–1111 (1976).

Tetrahedron Letter, vol. 33, No. 10 10, pp. 1285–1288, 1992 An Expedient Access To Trifluoro)Methyl Ketones From Carboxylic Acids, J. Bolvin et al.

Primary Examiner—José G. Dees
Assistant Examiner—Barbara S. Frazier
Attorney, Agent, or Firm—Thomas D. Rogerson; Jordan J. Driks

[57] ABSTRACT

A polyfluoro beta-keto ester is prepared by reacting a polyfluoro acid anhydride or a polyfluorocarboxylic acid chloride with a carboxylic acid chloride in the presence of a tertiary amine.

7 Claims, No Drawings

PROCESS FOR PREPARATION OF FLUORINATED BETA-KETO ESTER

BACKGROUND OF THE INVENTION

This invention relates to a process for making a beta-keto ester. More particularly, this invention relates to a process for making a beta-keto ester which is useful in preparing a 2-arylpyrimidine. 2-Arylpyrimidines are useful as both pre-emergent and post-emergent herbicides. They are particularly useful against monocot weeds such as Barnyardgrass, Crabgrass, Foxtail, Wild oat and the like and Dicot weeds such as Cocklebur, Morning glory, Nightshade, Velvetleaf and the like.

The 2-arylpyrimidines may be prepared by reacting a N-alkylamidine with a beta-keto ester. The keto ester, such as alpha-alkyl-polyfluoro-beta-keto ester, is generally synthesized by a Claisen condensation reaction using sodium hydride. In a commercial preparation, the use of sodium hydride for preparing the aforesaid beta-keto ester is undesirable because it is dangerous to work with on a large scale and presents the hazard of large amounts of explosive hydrogen gas.

It is an object of this invention therefore, to provide a process for preparing a beta-keto ester which may be used to prepare a 2-arylpyrimidine without the use of sodium hydride.

Another object of this invention is to provide a safe process for preparing a 2-arylpyrimidine using a beta-keto ester which does not utilize sodium hydride as a reactant.

Other objects and advantages will become apparent front the following more complete description and claims.

SUMMARY OF THE INVENTION

This invention relates to a process for making a 2-arylpyrimidine by reacting an N-alkylamidine with a beta-keto ester wherein the beta-keto ester has been prepared by reacting a polyfluorocarboxylic acid anhydride or a polyfluorocarboxylic acid chloride with a carboxylic acid chloride in the presence of a tertiary amine.

DETAILED DESCRIPTION

The desired 2-arylpyrimidines may be prepared by direct condensation of N-alkylamidine and a beta-keto ester by warming the reactants in an organic solvent such as methylene chloride, diethyl ether and the like, or by reaction of the reactants neat.

The beta-keto ester is prepared by reacting a polyfluoro-acid anhydride (II) or a polyfluorocarboxylic acid chloride (I) with a carboxylic acid chloride (III) in the presence of a tertiary amine.

The reaction may be carried out in the presence of a solvent such as methylene chloride, tetrahydrofuran, ethyl ether and the like or may be accomplished neat. If no solvent is present, the reaction may solidify. The reaction is quenched with alcohol to synthesize alpha-alkyl polyfluoro-beta-keto ester (IV).

After the reaction is complete, a solvent such as methylene chloride is then added and the reaction mixture is poured into a separatory funnel, washed with acid, washed with a base and then dried to yield a final product. The final product may then be used as the intermediate to react with N-alkylamidine to yield the herbicide, a 2arylpyrimidine, or the final product may be purified by distillation.

The preparation of the beta-keto ester is best summarized by the following equation:

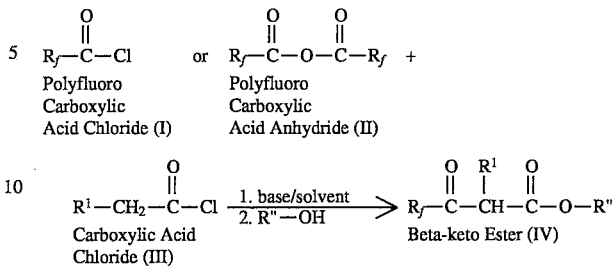

In the formula set forth above, $R_f$ may be a polyfluoroalkyl such as trifluoromethyl, pentafluoroethyl, heptafluoropropyl, heptafluoroisopropyl, difluoromethyl, 1,2,2,2-tetrafluoroethyl, 1,2,2,3,3,3-hexafluoropropyl and the like. The polyfluorocarboxylic acid anhydride (II) used in the process of this invention may be trifluoroacetic anhydride, perfluoropropionic anhydride, perfluorobutyric anhydride, difluoroacetic anhydride, 2,3,3,3-tetrafluoropropionic anhydride, 2,3,3,4,4,4-hexafluorobutyric anhydride, and the like. The polyfluorocarboxylic acid chlorides (I) used in the process of this invention may be such as trifluoroacetyl chloride, per fluoropropionyl chloride, perfluorobutyryl chloride, difluoroacetyl chloride, 2,333 tetrafluoropropionyl chloride, 2,3,3,4,4,4-heptafluorobutyryl chloride and the like.

The R' of the carboxylic acid chloride (III) may be hydrogen or a $C_1$ to $C_6$ straight or branched alkyl group. Thus, one may use a carboxylic acid chloride such as butyryl chloride, propionyl chloride, valeryl chloride, hexanoyl chloride, isovaleryl chloride, and the like.

One equivalent of the carboxylic acid chloride (III) is reacted with from 1 to about 8 equivalents of the polyfluoro carboxylic acid chloride (I) or of the polyfluoro carboxylic acid anhydride (II). It is preferred however that 1 equivalent of the carboxylic acid chloride (II) be reacted with about 1.1 equivalents of the acid chloride (I) or of the anhydride (II).

The R" of the beta-keto ester (IV) is the same as the R" of the alcohol which is used to quench and complete the reaction. R" may be a $C_1$ to $C_6$ straight or branched alkyl groups such as methyl, ethyl, propyl and the like.

The reaction of the acid chloride (I) or acid anhydride (II) with carboxylic acid chloride (III) is preferably carried out in the presence of a solvent for the reactants such as a halogenated hydrocarbon, ether or aromatic solvent. Among the solvents which may be used are chloroform, methylene chloride, diethyl ether, and tetrahydrofuran. It is preferred however, that the solvent which is used be a halogenated solvent and it is especially preferred that the solvent used be methylene chloride.

The amount of solvent used is not critical but is generally used in an amount such that the reactants will be dissolved therein and the reaction product may easily be obtained therefrom.

In conducting the reaction, a tertiary amine is present. The tertiary amine may generally be used in an amount of from about 1 to about 8 equivalents based on the carboxylic acid chloride (III) and preferably in an amount of from about 2 to about 4 equivalents.

Any tertiary amine may be used in practicing this reaction such as pyridine, quinoline, isoquinoline, N-methylpyrrole, alkyl substituted pyridines such as lutidine, and the like or a trialkyl amine, wherein each alkyl of the trialkyl portion may be the same or different, having from 1 to 12 carbon atoms such as triethylamine, trimethylamine, N,N-diethyl-N-methylamine and the like. It is preferred however, that the base used be pyridine.

An alcohol is used to quench and complete the reaction and is the final step in the synthesis of the beta-keto ester.

Any alcohol may be used to quench the reaction and complete the synthesis. Generally speaking, the alcohol used may vary from methanol to hexanol or even a higher alcohol may be used. The choice of alcohol is dictated only by practical considerations. It is preferred however, that the alcohol which is used be ethyl or methyl alcohol. Other alcohols such as propyl and butyl may also be used.

The alcohol is used in an amount of I to about 10 equivalents based on the carboxylic acid chloride (III).

In practicing the process of this invention, the solvent, polyfluoro carboxylic acid anhydride (II) or polyfluoro carboxylic acid chloride (I) and carboxylic acid chloride (III) is added to a reaction vessel. The tertiary amine, which has been dried, is then added to the reaction mixture. The reaction is exothermic. The temperature of the reaction mixture is maintained between about −50° C. to about 20° C. and preferably from about −10° C. to about 20° C. and most preferably from about 10° C. to about 12° C.

After the addition of the base is completed, additional solvent may be added to the reaction mixture. The reaction mixture is maintained at the temperature of between about 15° C to about 25° C. and is stirred for from about 3 to about 5 hours. The reaction is then cooled to about 0° C. to about −10° C. and alcohol is then added to quench the reaction. The alcohol is added dropwise so as to maintain the temperature at 0° C. or below. The mixture is then stirred and allowed to warm to room temperature.

The time elapsed before the addition of the alcohol to the reaction is dependent upon the number of equivalents of the reactants used and the particular reactants and solvents used. Reactions which use minimal amounts of the fluorinated anhydride (II) and base may run from 0.5 hour to 24 hours before the addition of the alcohol. The process may also be carried out from about 1 to about 16 hours and preferably, the alcohol is added when 3 to about 5 hours of time has elapsed.

If one were to use a large excess of the fluorinated anhydride and base, the reaction time could be decreased to even less time before the addition of the alcohol.

The amount of the reactants used (polyfluoroacid anhydride (II) or polyfluorocarboxylic acid chloride (I)) may vary. Generally, it is preferred to use an excess of the anhydride or polyfluorocarboxylic acid chloride over stoichiometry because it has been found that the purity and yield of the reaction product is enhanced.

In order to more fully illustrate the nature of this invention and the manner of practicing the same, the following examples are presented.

EXAMPLE 1

Preparation of Ethyl 2-(trifluoroacetyl)butanoate Using Trifluoroacetic Anhydride To a one liter three neck round bottom flask, equipped with a magnetic stirrer, nitrogen inlet, addition funnel and thermometer is charged 50 mL (0.482 mol) of butyryl chloride and 300 mL of methylene chloride. To this is added 70.14 mL (0.496 mol) of trifluoroacetic anhydride. The trifluoroacetic anhydride is added in a single portion to the reaction mixture. The flask is cooled with an ice water bath to 10° C. and 80 mL (0.989 mol) of pyridine, which has been dried over sodium hydroxide pellets, is added at a rate sufficient to maintain the temperature of the reaction mixture between 10° C. and 12° C. When the pyridine addition is complete, 50 mL of methylene chloride from the addition funnel is added to the reaction mixture. The reaction mixture is maintained at its temperature of about 10° C. for an additional 15 minutes. The ice bath is then removed and the reaction is stirred for three hours at room temperature. The reaction is then cooled to 0° C. or slightly below. Then 80 mL of cold absolute ethanol is added dropwise. During the addition, the temperature of the reaction mixture is maintained at 0° C. The mixture is then stirred and allowed to warm to room temperature overnight.

The reaction mixture is then poured into a separatory funnel and is washed three times with 3M hydrochloric acid, once with water, and three times with saturated aqueous sodium bicarbonate. The organic layer is separated and is dried using magnesium sulfate and is placed on a rotary evaporator using a 22° C. water bath to yield 63.15 grams of ethyl 2-(trifluoroacetyl) butanoate as a yellow liquid which is then fractionally distilled through a Vigreux column at 60 mm mercury to afford ethyl 2-(trifluoroacetyl)butanoate as a clear colorless liquid boiling between 60° C. and 85° C.

EXAMPLE 2

Preparation of Ethyl 2-(trifluoroacetyl)butanoate Using Trifluoroacetyl Chloride To a one liter, three neck, round bottomed flask, equipped with a magnetic stirrer, nitrogen inlet, addition funnel and thermometer is charged 5 mL (0.048 mol) of butyryl chloride and 35 mL of methylene chloride. The solution is cooled to −5° C. and 40 mL of 1.32M trifluoroacetyl chloride in methylene chloride is added. Pyridine, 8 mL, is then quickly added. The ice bath is removed and the reaction mixture is stirred at room temperature for one hour. The reaction mixture is then cooled to 0° C. and 40 mL of ice cold absolute ethanol is added. After stirring the reaction mixture for 16 hours at room temperature, the methylene chloride solvent is removed under vacuum. Ethyl ether is then added to the residue. The reaction mixture is then poured into a separatory funnel and is washed three times with 3M hydrochloric acid followed by three successive washings with saturated sodium bicarbonate. The organic layer is separated, dried over magnesium sulfate and concentrated, under vacuum, to yield 4.8 grams of crude ethyl 2-(trifluoroacetyl)butanoate, as a liquid.

EXAMPLE 3

Preparation of Methyl 2-difluoroacetylbutanoate

To a one liter, three neck, round bottomed flask equipped with a magnetic stirrer, nitrogen inlet, addition funnel and thermometer is charged a solution of 25 mL (0.24 mol) of butyryl chloride in 200 mL of methylene chloride. Next, 43.53 mL (0.25 mol) of difluoroacetic anhydride is added in one portion. The reaction mixture is then cooled, using an ice bath, to 0° C. and 40 mL (0.5 mol) of pyridine is then added dropwise over a period of thirty minutes. The ice bath is then removed and the reaction is stirred for 5 hours at room temperature. The reaction is cooled to −10° C. and 40 mL of methanol is then added to the reaction mixture over a period of 15 minutes. The reaction mixture is allowed to warm to room temperature overnight, with stirring. The solvent is removed from the reaction mixture using a rotary evaporator and ethyl ether is then added to the residue. The organics are then poured into a separatory funnel and washed two times with 5% hydrochloric acid and twice with saturated sodium bicarbonate. The organic layer is then dried over magnesium sulfate and is concentrated to yield 28.29 grants of a yellow liquid product. The crude product is then distilled using a 10 cm Vigreux column at 25 mm mercury. A single fraction, having a boiling point of between 65° to 75° C., yielded 11.41 gms of methyl 2-(difluoroacetyl)butanoate as a clear colorless liquid of 80% purity.

EXAMPLE 4

Preparation of Ethyl 2-(trifluoroacetyl)propionate

To a one liter, 3 neck, round bottomed flask, equipped with a magnetic stirrer, nitrogen inlet, addition funnel and thermometer is charged 44 mL (0.51 mol) of propionyl chloride and 350 mL of methylene chloride. To this solution is added 70 mL (0.5 mol) of trifluoroacetic anhydride. The flask is then cooled with an ice bath until the solution temperature is 10° C. Next, 80 mL (0.99 mol) of pyridine which had been dried over sodium hydroxide pellets, is added dropwise over a period of 45 minutes. During the addition, the reaction temperature is kept below 15° C. The ice bath is removed after 15 minutes and the reaction is stirred at room temperature for an additional 3.5 hours. The reaction is then cooled to −20° C., using a dry ice/aqueous calcium chloride bath. Absolute alcohol, 80 mL, is then added over a period of 15 minutes. The reaction mixture is stirred for 2.5 hours at room temperature. Methylene chloride is added to the reaction mixture and the reaction mixture is poured into a separatory funnel. The organic layer is washed two times with 5% hydrochloric acid and two times with saturated sodium bicarbonate. The organic layer is dried over magnesium sulfate and the solvent in the organic layer is then removed using a vacuum, to yield 52.14 grams of a brown liquid product. The crude product is distilled using a 10 cm Vigreux column at 55 mm mercury. Three fractions, boiling within 50° to 68° C., are obtained and combined and dissolved in ethyl ether and again washed with 5% hydrochloric acid and saturated sodium bicarbonate. The organic layer is dried and concentrated to yield 15.31 grams of a mixture which is approximately 2:1 of ethyl 2-(trifluoroacetyl)propionate and ethyl 3,3-dihydroxy-2-methyl-4,4,4-trifluorobutyrate, respectively, as a clear colorless oil. The equilibrium for the reaction product may be represented by the formula:

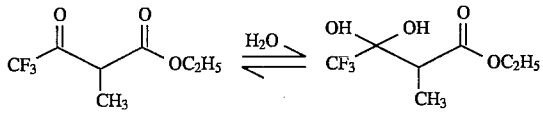

While this invention has been described in terms of certain preferred embodiments and illustrated by means of specific examples, the invention is not to be construed as limited except as set forth in the following claims.

I claim:

1. In a process for making a 2-arylpyrimidine by reacting a N-alkylamidine with a beta-keto ester, the improvement comprising preparing the beta-keto ester by reacting a polyfluorocarboxylic acid chloride conforming to the formula;

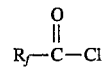

wherein $R_f$ is selected from a polyfluoroalkyl, is reacted with a carboxylic acid chloride in the presence of a tertiary amine.

2. The process according to claim 1, wherein the polyfluoroalkyl is selected from pentafluoroethyl, heptafluoropropyl, heptafluoroisopropyl, difluoromethyl, 1,2,2,2-tetrafluoroethyl, 1,2,2,3,3,3-hexafluoropropyl, and trifluoromethyl.

3. The process according to claim 1, wherein said polyfluorocarboxylic acid chloride is selected from trifluoroacetyl chloride; perfluoropropionyl chloride; perfluorobutyl chloride; difluoroacetyl chloride; 2,3,3,3-tetrafluoropropionyl chloride; and 2,3,3,4,4,4-hexafluorobutyryl chloride.

4. The process according to claim 1, wherein said tertiary amine is selected from pyridine; lutidine; quinoline; isoquinoline; and N-methyl pyrrole.

5. The process according to claim 1, wherein said tertiary amine is a trialkylamine wherein each alkyl portion has from 1 to 12 carbon atoms and each alkyl of the trialkyl portion may be the same or different.

6. The process according to claim 1, wherein said tertiary amine is selected from triethylamine; trimethylamine; and diethylmonomethylamine.

7. The process according to claim 1, wherein the beta-keto ester is represented by the formula;

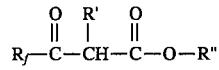

and $R_f$ is difluoromethyl or trifluoromethyl, R' is ethyl or methyl and R" is ethyl or methyl.

* * * * *